(12) United States Patent
Koest et al.

(10) Patent No.: US 6,286,958 B1
(45) Date of Patent: Sep. 11, 2001

(54) DEVICE FOR THE EXAMINATION OF AN EYE USING A SCHEIMPFLUG CAMERA AND A SLIT LIGHT PROJECTOR FOR PHOTOGRAPHING SLIT IMAGES OF AN EYE

(75) Inventors: Gert Koest, Hannover; Marc Repnow, Bremen, both of (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 09/626,321

(22) Filed: Jul. 26, 2000

(30) Foreign Application Priority Data

Aug. 4, 1999 (DE) .......................................... 299 13 602 U

(51) Int. Cl.[7] ...................................................... A61B 3/10
(52) U.S. Cl. .............................................................. 351/214
(58) Field of Search .................................... 351/206, 208, 351/211, 212, 214, 245, 246; 600/558

(56) References Cited

U.S. PATENT DOCUMENTS

| | | |
|---|---|---|
| 4,171,877 | 10/1979 | Karasawa et al. . |
| 5,870,167 * | 2/1999 | Knopp ................................... 351/212 |
| 5,886,767 * | 3/1999 | Snook ................................... 351/212 |
| 5,886,768 | 3/1999 | Knopp et al. . |

OTHER PUBLICATIONS

"Development of a New Equipment for Rotating Slit Image Photography According to Scheimpflug's Principle", V. Dragomirescu, O. Hockwin, H.-R. Koch and K. Sasaki, 1978, pp. 118–130.

* cited by examiner

*Primary Examiner*—George Manuel
(74) *Attorney, Agent, or Firm*—Flynn, Thiel, Boutell & Tanis, P.C.

(57) ABSTRACT

The invention relates to a device for the examination of an eye using a Scheimpflug camera and a slit light projector for slit images of an eye. The Scheimpflug camera and the slit light projector are carried by a stand, whereby the slit light projector and the scheimpflug camera are arranged rotatably about a common axis coinciding essentially with the optic axis of the eye. Such a device is improved so that without interruptions and returns of the Scheimpflug camera to an initial position, the eye can be scanned multiply by means of the device. This is achieved by the slit light projector and the Scheimpflug camera being freely rotatable about the axis through more than 360°, and by a voltage supply to both the Scheimpflug camera and the slit light projector occurring through a transmitter.

24 Claims, 5 Drawing Sheets

Fig. 3
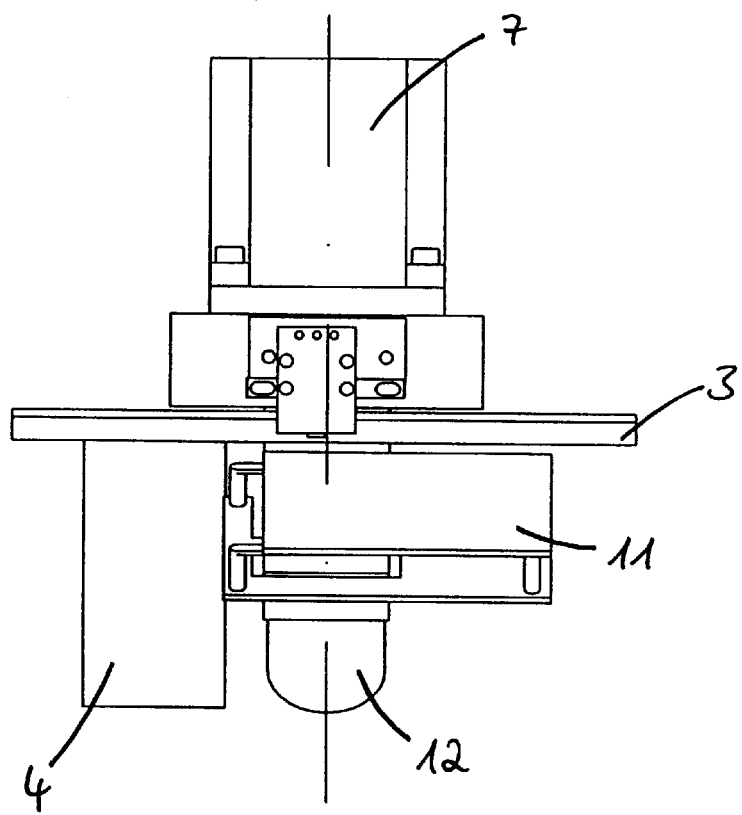
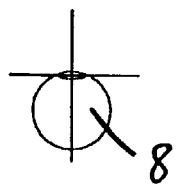

DEVICE FOR THE EXAMINATION OF AN EYE USING A SCHEIMPFLUG CAMERA AND A SLIT LIGHT PROJECTOR FOR PHOTOGRAPHING SLIT IMAGES OF AN EYE

FIELD OF THE INVENTION

The invention relates to a device for the examination of an eye using Scheimpflug camera and a slit light projector for photographing transverse sections or slit images of an eye, all of which is carried by a stand, whereby the slit projector and the scheimpflug camera are arranged rotatably about a common axis, which coincides essentially with the optic axis of the eye.

BACKGROUND OF THE INVENTION

Devices for the examination of an eye using a Scheimpflug camera offer the possibility for diagnosis of the front chamber of the eye. Basically they offer a special form of the slit lamp examination, whereby the illuminated plane of the eye using a Scheimpflug camera namely has a slit projector, as it can also be used in common slit lamps.

Such slit projectors are known from the state of the art. The principle of the slit projector is based on the refraction media of the front chamber of the eye not being clear but instead thereat, in particular in the shortwave potion of the visible light, occurs a clear scattering. This has the result that a strongly concentrated light beam, namely the projected slit light, which is sent through the optic media of the eye, when viewed laterally, becomes visible in the media, similar to light beams of automobile headlights in fog. The various portions of the refraction media of the eye have a differently strong light scattering capability and can therefore be differentiated. The principle of this focal illumination is perfected in the slit projector. A slit-shaped luminous beam of a high brightness and as high as possible color temperature is being used for the illumination.

The plane in the eye illuminated by means of the slit projector can be photographed by means of a Scheimpflug requirement. A Scheimpflug camera is a camera, which meets the Scheimpflug requirement. The Scheimflug requirement demands that the plane of the object points, this is here the illuminated plane in the eye, the main plane of the camera lens system and the image plane intersect in a common axis. By tilting the image plane relative to the main plane of the camera lens system, it is possible for the object plane to be in any desired special position, whereby object points can be detected in the depth of sharpness zone, which object points at a vertical object plane cannot at the same time be sharply reproduced.

Such a device is known, for example, also from the U.S. Pat. No. 4,171,877. The disadvantage of the device disclosed in this reference is that the voltage supply and also the data transfer occurs by means of cable. Furthermore rotationally fixed parts of the Scheimpflug camera are mounted in such a manner that they lie in the path of rotation of rotatable parts of the Scheimpflug camera. This limits the rotating ability of the Scheimpflug camera and of the slit light projector. This has the disadvantage that a relatively expensive control must be provided for the rotating movement of the Scheimpflug camera and of the slit light projector so that, for example, the cable for the voltage supply or the data transfer are not torn. A multiple scanning of the eye is thus always interrupted by a return of the Scheimpflug camera and of the slit light projector into an initial position. Thus again and again bothersome interruptions occur during the examination of an eye, which interruptions are caused by the mechanical design of an eye, which interruptions are caused by the mechanical design of the Scheimpflug camera.

The basic purpose of the invention is therefore to provide a device for the examination of an eye, with which without interruptions and returns to an initial point the eye can be multiply scanned.

This purpose is attained according to the invention by the slit light projector and the Scheimpflug camera being freely rotatable about the axis for more than 360°, and by a voltage supply to both the Scheimpflug camera and the slit light projector occurring through a transmitter.

A wireless connection to the voltage supply, the Scheimpflug camera and/or the slit light projector is made possible by the transmitter of the invention. The angle of rotation of the Scheimpflug camera and of the slit light projector is therefore no longer limited by cable. By multiple rotations of the slit light projector and of the Scheimpflug camera the eye can thus be scanned in a quick sequence and the slit images can be photographed.

The transmitter is according to the invention a sliding ring transmitter. The Scheimpflug camera and the slit light projector are advantageously mounted on a rotor rotatably supported on the stand, whereby the axis of rotation of the rotor is the optic axis of the slit projector. According to the invention it is then possible to mount a computer unit on the rotor, which computer unit is connected to the scheimpflug camera.

According to the invention a wireless data transfer path can exist to the Scheimpflug camera and/or the computer unit. This wireless data transfer path can advantageously be guided over the sliding ring transmitter. Just like the voltage supply by means of a transmitter, the wireless data transfer path is suited for the Scheimpflug camera with the slit light projector being able to be rotatable through any desired angle. Due to the fact that a computer unit is already installed on the rotor, a large portion of the needed data processing of the image data delivered by the Scheimpflug camera can already take place in said computer. In particular when, as it is particularly advantageous, a CCD-camera or C-MOS-camera is used, the digital signal of the computer unit, which signal is delivered by these cameras, can be converted into an analogous signal, with the result that only two electric signals must be guided through the transmitter instead of the 16 signals common for a digital coding.

The stand of a Scheimpflug camera of the invention can be advantageously moved about three orthogonal axes.

The slit light projector has in a particular embodiment of the Scheimpflug camera a light source, a slit diaphragm arranged in front of the light source, and a lens system arranged in front of the slit diaphragm. The light source consists thereby of several illuminating diodes arranged side-by-side and essentially in longitudinal direction of the slit, namely in the plane of the projected slit.

The inventive use of illuminating diodes as a light source in the Scheimpflug camera has many advantages. The most important advantage for the ophthalmologist is the high speed, with which the flashes needed for slit image photography can be produced with the illuminating diodes. Moreover, illuminating diodes are significantly compacter than the common light sources; the illuminating diodes are more robust than, for example, highly sensitive Xenon-high-pressure lamps and noticeably less expensive.

The illuminating diodes of the Scheimpflug camera can according to the invention be arranged arc-shaped or circularly in this special design. The curvature of the arc is then advantageously determined such that an as large as possible amount of light passes through the lens system. However, it is also possible that in the special design of the Scheimpflug camera the illuminating diodes are arranged essentially in a plane parallel to the slit diaphragm. The main beams of the illuminating diodes are then advantageously inclined relative to the optic axis of the lens system, and the inclination of the main beams corresponds with the distance of the illuminating diodes from the optic axis. The main beams intersect advantageously in one common point of intersection.

The slit light projector can in the special design of the inventive scheimpflug camera have advantageously a second slit diaphragm in front of the lens system, whereby the slit of this second slit diaphragm is coaxial and aligned with the slit of the first slit diaphragm.

The illuminating fields of the illuminating diodes can according to the invention consist of illuminating diode chips. These illuminating diode chips are then advantageously arranged along a straight line, whereby the connecting fields lie on both sides of the straight line. With this arrangement of the illuminating diode chips it is achieved that the areas of the illuminating diode chips, which areas are uncovered by the connected fields, lie as much as possible at the edge of the illuminating fields reproduced on the first slit diaphragm, and an as large as possible amount of light reaches the lens system.

The diode lenses can according to the invention be astigmatic and/or the lens system can consist of cylinder lenses. A concentration of the light produced by the illuminating fields on the slit in the first slit diaphragm is achieved in both cases.

The first slit diaphragm can according to the invention have a width of 50 to 120 $\mu$m, whereas the aperture angle of the concentration of beams exiting from this first slit diaphragm is not supposed to be larger than 2.9°. In order to obtain an advantageous scattering behavior, illuminating diodes, which produce a blue light, are preferred.

BRIEF DESCRIPTION OF THE DRAWINGS

One exemplary embodiment of the invention will be described in greater detail in connection with the drawings, in which:

FIG. 3 is a top view of the device according to FIG. 1.

DETAILED DESCRIPTION

Figure 1:
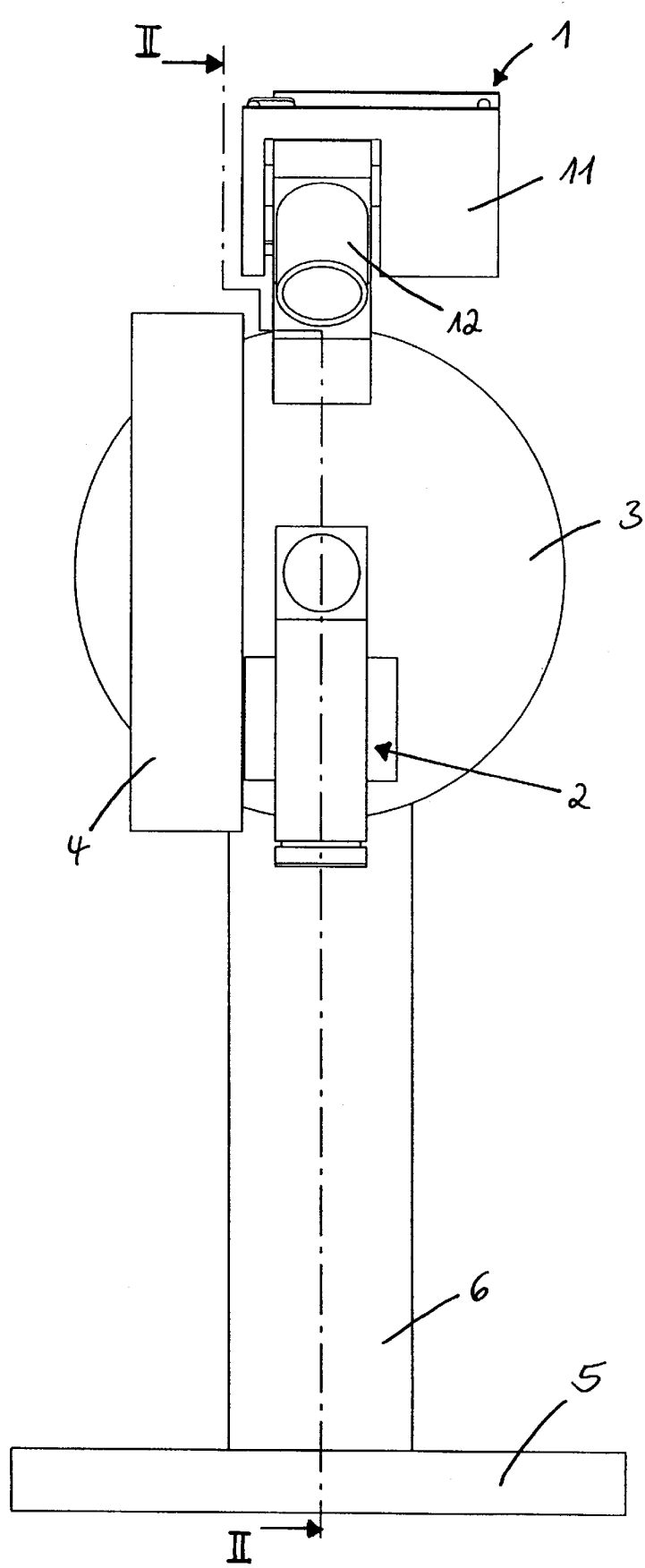
FIG. 1 is a front view of a device of the invention.
Figure 2:
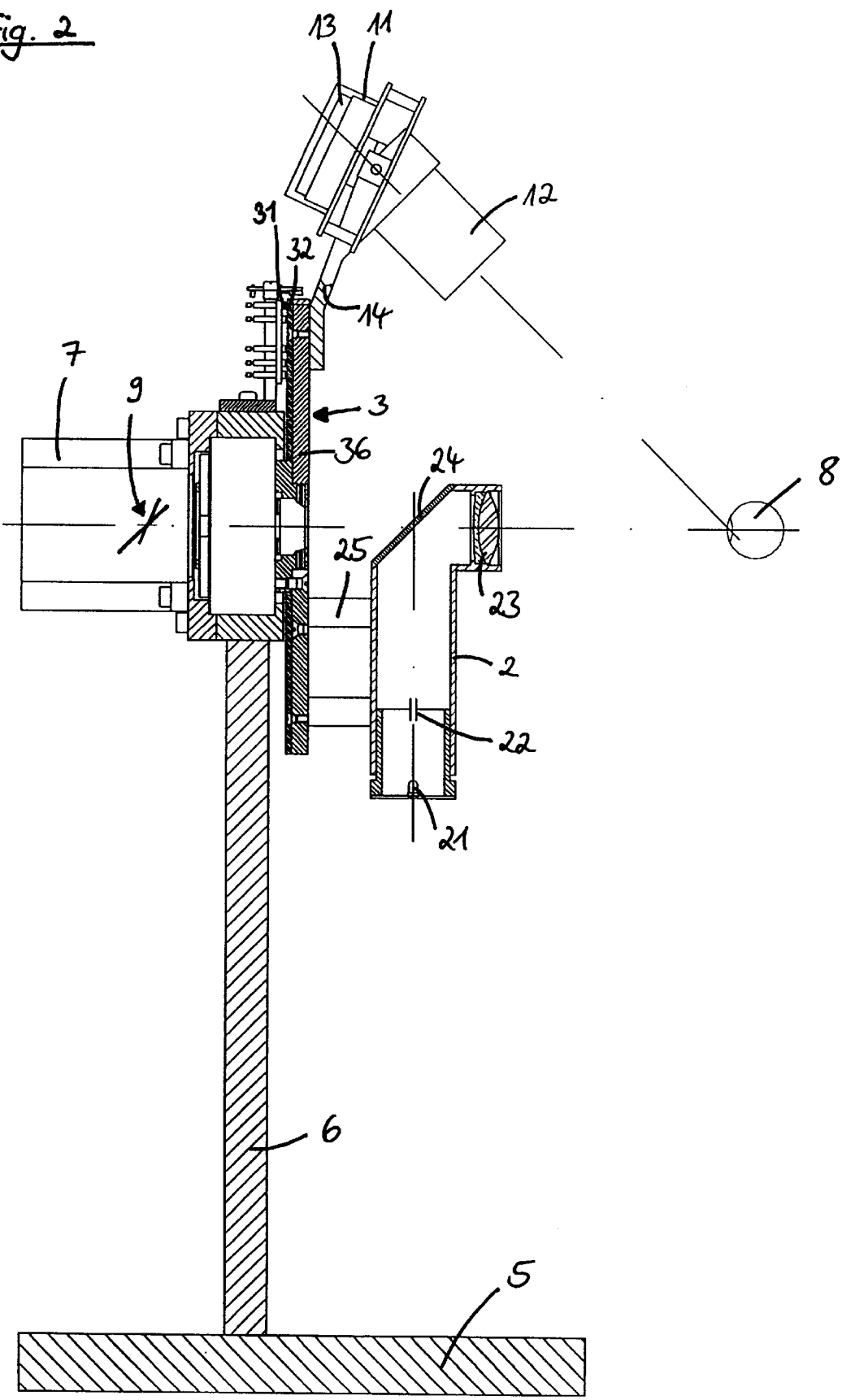
FIG. 2 is a lateral cross-sectional view of the device along the line II, II of FIG. 1.
Figure 4:
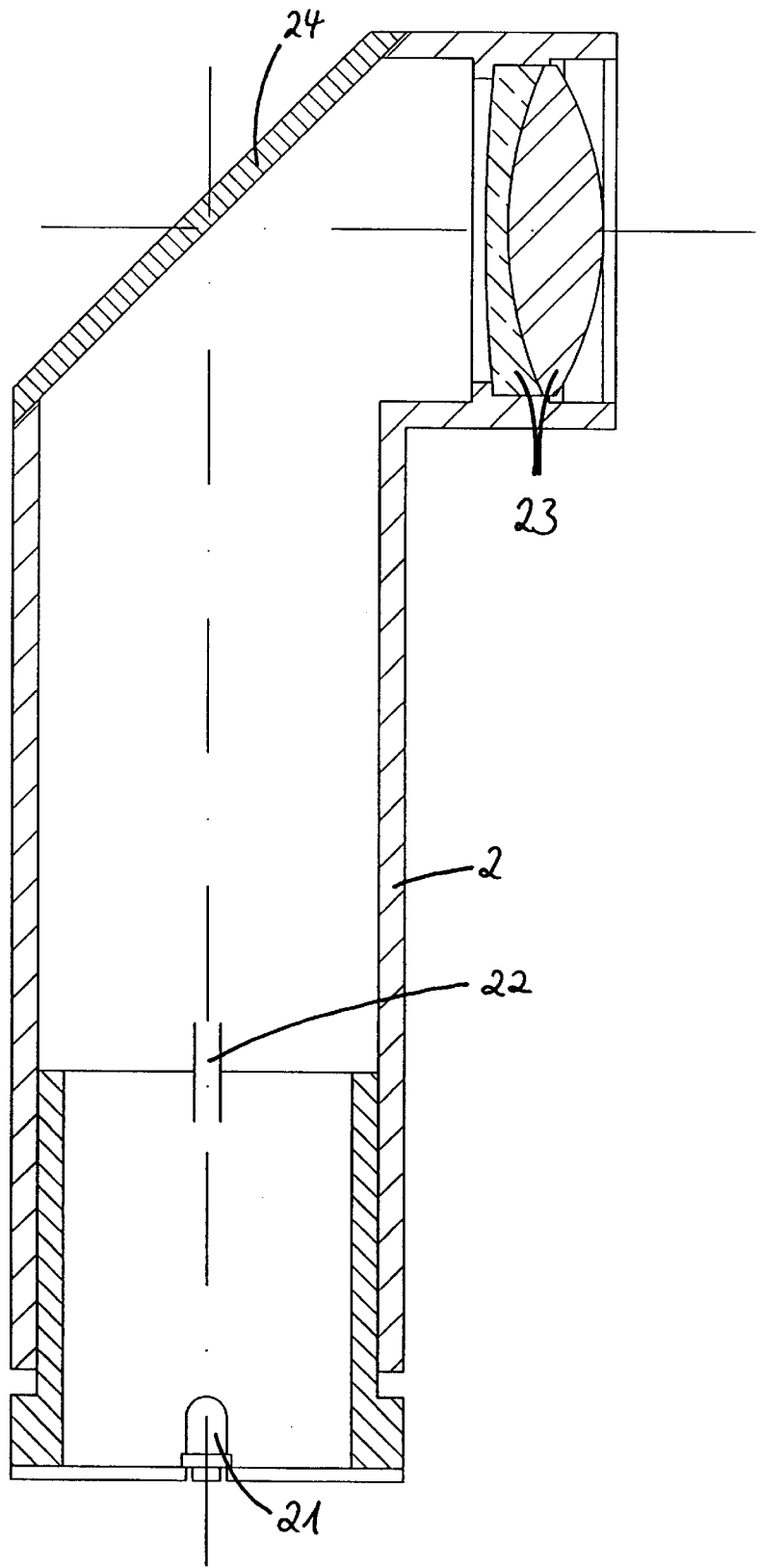
FIG. 4 illustrates the slit light projector of a Scheimpflug camera according to FIGS. 1 to 3.
Figure 5:
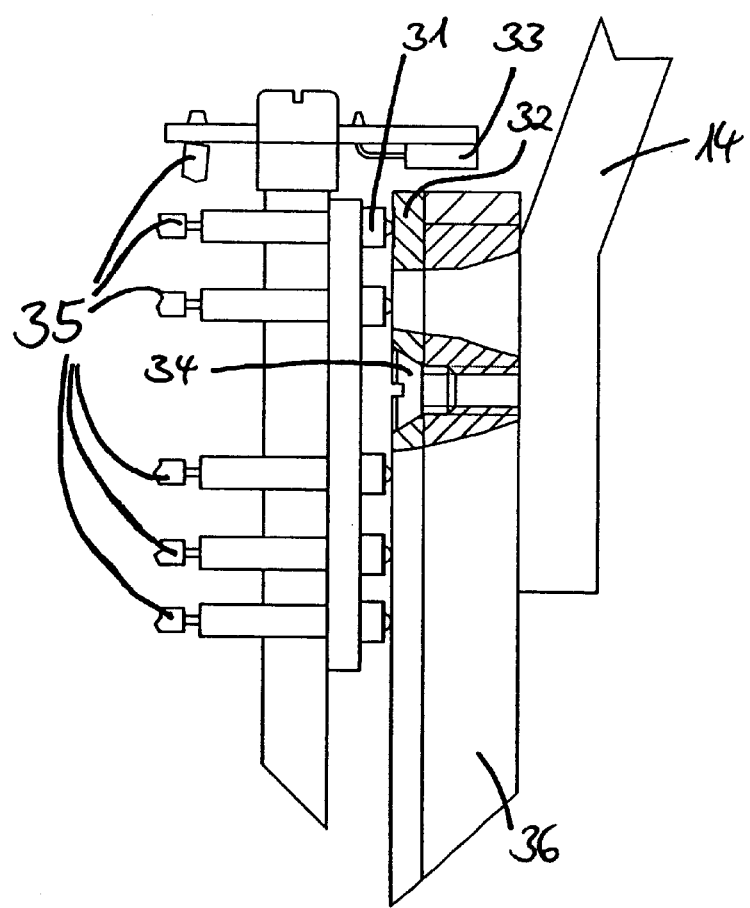
FIG. 5 illustrates a detail of the sliding ring transmitter of the device according to FIGS. 1 to 3.

The device of the invention with a Scheimpflug camera 1 and a slit light projector 2 has a stand 6, which rests on a base 5. A rotor 3 is rotatably supported on the stand 6. The rotor 3 can be driven by a motor 7. The motor 7 is preferably a stepping or indexing motor.

The Scheimpflug camera 1 and the slit light projector 2 are in turn respectively fastened to the rotor 3 through a holder 14 and a holder 25. The optic axis of the beams exiting from the slit light projector 2 coincides thereby with the axis of rotation of the rotor.

The slit light projector 2 has as the light source a row of diodes 21. This row of diodes 21 illuminates a slit diaphragm 22, so that said slit diaphragm is reproduced according to the Koehler imaging scheme through a mirror 24 in the projector lens System 23. The light entering through the slit of the slit diaphragm 22 is concentrated there in order to finally illuminate a plane in the eye 8 of a patient. This plane can now be photographed by means of a Scheimpflug camera 1. The Scheimflug camera 1 has for this purpose a camera lens system 12, which is mounted in front of the housing 11 of the Scheimpflug camera. A CCD-chip is arranged in the housing 11 of the Scheimpflug camera 1 in the image plane 13, with which CCD-chip the image is received. In order to satisfy the Scheimpflug requirement, the image plane 13, the main plane of the camera lens system 12 and the viewed and illuminated plane are thereby inclined with respect to one another in the eye 8 of the patient in such a manner that they intersect in one common axis 9.

The picture taken by the Scheimpflug camera is converted into an analogous video signal in the computer unit 4 mounted on the rotor 3. This analogous video signal is guided onto two sliding rings 32, which are fastened on the rotor 3 by means of screws 34. Furthermore, sliding ring contacts 31 are fastened on the stand 6, with which sliding ring contacts the video signal is taken from the sliding rings 32. The video signal travels then through connecting lines 35 to a not illustrated calculator and/or monitor. In addition to the two sliding ring transmitters for the video signal, three further sliding rings 32 or three further sliding contacts 31 are provided on the rotor 3 or on the stand 6, with which voltage is supplied to the slit light projector 2 and to the Scheimpflug camera 1. Furthermore, a sensor 33 is mounted on the stand 6., which sensor 33 measures the angle of rotation of the rotor 3 with the Scheimpflug camera 1 and the slit light projector 2. Thus it is possible to determine directly, in which angular position the Scheimpflug camera and the slit light projector 2 is with respect to the initial position.

The advantage of this exemplary embodiment of a device of the invention is that because of the sliding ring transmitter any desired angles of rotation of the rotor and thus of the Scheimpflug camera and of the slit light projector can be traveled. Thus the entire eye can be scanned and this also without having to return the Scheimpflug camera or the slit light projector into the initial position. Also a multiple scanning of the eye is possible. The scanning occurs significantly faster than in devices of the state of the art since the slit light projector by being equipped with illuminating diodes as illuminating sources, in contrast to the illuminating sources common in the state of the art, can ignite very quick and bright flashes. The illustrated device can moreover be manufactured less expensive than the Scheimpflug camera common in the state of the art. By doing away with sensitive Xenon high pressure lamps, the slit light projection can be designed significantly compacter since an additional cooling device is not needed.

What is claimed is:

1. A device for the examination of an eye using a Scheimpflug camera and a slit light projector for photographing slit images of an eye, all of which is carried by a stand, whereby the slit light projector and the Scheimpflug camera are arranged rotatably about a common axis coinciding essentially with the optic axis of the eye, wherein the slit light projector and the scheimpflug camera are freely rotatable about the axis for more than 360°, and that a voltage supply to both the Scheimpflug camera and the slit light projector occurs through a transmitter.

2. The device according to claim 1, wherein the transmitter is a sliding ring transmitter.

3. The device according to claim 2, wherein a data transfer path to the scheimflug camera, the slit light projector and/or the computer unit exists through the sliding ring transmitter.

4. The device according to claim 1, wherein the Scheimpflug camera and the slit light projector are mounted on a rotor rotatably supported on the stand, the axis of rotation of which rotor is the optic axis of the slit light projector.

5. The device according to claim 4, wherein a computer unit is mounted on the rotor, which computer is connected to the Scheimpflug camera.

6. The device according to claim 1, wherein a wireless data transfer path connected to the scheimpflug camera, the slit light projector and/or the computer unit exists.

7. The device according to claim 1, wherein the Scheimpflug camera is a CCD-camera.

8. The device according to claim 1, wherein the Scheimflug camera is a C-MOS-camera.

9. The device according to claim 1, wherein the stand can be moved in three space axes.

10. The device according to claim 1, whereby the slit light projector has a light source, a slit diaphragm arranged in front of the light source, and a lens system arranged in front of the slit diaphragm, wherein the light source consists of several illuminating diodes arranged side-by-side and essentially in longitudinal direction of the slit, namely in the plane of the projected slit.

11. The device according to claim 10, wherein the illuminating diodes are arranged archlike or circularly in the plane of the projected slit.

12. The device according to claim 10, wherein the illuminating diodes are arranged paraaxially with respect to the slit diaphragm.

13. The device according to claim 12, wherein the main beams of the illuminating diodes are inclined relative to the optic axis of the lens system, and the inclination of the main beams corresponds with the distance of the illuminating diodes from the optic axis.

14. The device according to claim 13, wherein the main beams of the illuminating diodes intersect essentially in one common point.

15. The device according to claim 10, wherein a second slit diaphragm is arranged in front of the lens system, whereby the slit of the second slit diaphragm is aligned with the slit of the first slit diaphragm.

16. The device according to claim 10, wherein a second slit diaphragm is arranged in front of the lens system, whereby the slit of the second slit diaphragm is aligned with the slit of the first slit diaphragm.

17. The device according to claim 16, wherein the illuminating diode chips are arranged along a straight line, whereby the connecting fields lie on both sides of the straight line.

18. The device according to claim 10, wherein the lens system is astigmatic.

19. The device according to claim 10, wherein the lens system has cylinder lenses.

20. The device according to claim 10, wherein the illuminating diodes produce blue light.

21. The device according to claim 1, wherein a dichroic mirror is provided in the beam path of the light projector and/or the Scheimflug camera.

22. The device according to claim 21, wherein the curvature of the arc is determined such that as large as possible amounts of light pass through the lens system.

23. The device according to claim 1, wherein the slit of the first slit diaphragm has a width of 50 to 120 $\mu$m.

24. The device according to claim 1, wherein the aperture angle of the beam concentration exiting from the first slit diaphragm is no longer than 2.9°.

* * * * *